US008232090B2

(12) United States Patent
Kallenmareth et al.

(10) Patent No.: US 8,232,090 B2
(45) Date of Patent: Jul. 31, 2012

(54) **STRAIN OF *SCHIZOCHYTRIUM LIMACINUM* USEFUL IN THE PRODUCTION OF LIPIDS AND EXTRACELLULAR POLYSACCHARIDES AND PROCESS THEREOF**

(75) Inventors: Isaac Oomman Kallenmareth, Tamil Nadu (IN); Philip Oomman Kollenmareth, Tamil Nadu (IN); Rajni Sophia Vedamuthu, Tamil Nadu (IN); Kumar Lakshmana Arlagadda, Tamil Nadu (IN); Raghukumar Seshagiri, Dona Paula (IN)

(73) Assignee: ABL Biotechnologies Ltd., Chennai (IN)

( * ) Notice: Subject to any disclaimer, the term of this patent is extended or adjusted under 35 U.S.C. 154(b) by 1038 days.

(21) Appl. No.: 12/163,429

(22) Filed: Jun. 27, 2008

(65) Prior Publication Data

US 2009/0004219 A1 Jan. 1, 2009

Related U.S. Application Data

(63) Continuation of application No. PCT/IN2006/000508, filed on Dec. 28, 2006.

(30) Foreign Application Priority Data

| Dec. 29, 2005 | (IN) | 1948/CHE/2005 |
| Sep. 20, 2006 | (IN) | 1719/CHE/2006 |
| Sep. 20, 2006 | (IN) | 1720/CHE/2006 |

(51) Int. Cl.
*C12N 1/20* (2006.01)
*C12P 7/64* (2006.01)
*C12P 19/04* (2006.01)

(52) U.S. Cl. ............ 435/257.1; 435/134; 435/101
(58) Field of Classification Search ........... None
See application file for complete search history.

(56) References Cited

U.S. PATENT DOCUMENTS

| 5,130,242 | A | | 7/1992 | Barclay |
| 5,151,291 | A | * | 9/1992 | Tokairin et al. ........... 426/581 |
| 5,340,594 | A | | 8/1994 | Barclay |
| 5,340,742 | A | | 8/1994 | Barclay |
| 5,374,657 | A | | 12/1994 | Kyle |
| 5,518,918 | A | | 5/1996 | Barclay |
| 5,550,156 | A | | 8/1996 | Kyle |
| 5,688,500 | A | | 11/1997 | Barclay |
| 5,908,622 | A | | 6/1999 | Barclay |
| 5,985,348 | A | | 11/1999 | Barclay |
| 6,054,147 | A | | 4/2000 | Barclay et al. |
| 6,103,255 | A | | 8/2000 | Levene et al. |
| 6,177,108 | B1 | | 1/2001 | Barclay |
| 6,235,331 | B1 | * | 5/2001 | Kataoka et al. ........... 426/330.6 |
| 6,566,123 | B1 | | 5/2003 | Barclay |
| 6,582,941 | B1 | | 6/2003 | Yokochi et al. |
| 6,607,900 | B2 | | 8/2003 | Bailey et al. |
| 6,716,460 | B2 | | 4/2004 | Abril |

FOREIGN PATENT DOCUMENTS

| EP | 1 021 083 B1 | 5/2003 |
| EP | 0 669 809 B1 | 6/2003 |
| WO | WO 94/08467 A1 | 4/1994 |
| WO | WO 96/33263 A1 | 10/1996 |

OTHER PUBLICATIONS

Kamlangdee et al., Songklanakarin J. Sci. Technol., 2003, 25(5): 643-650.*
Franklin et al., Dietary Marine Algae (*Schizochytrium* sp.) Increases . . . , Article, 1999, 7 pages, American Society for Nutritional Sciences.
Yokochi et al., Optimization of docosahexaenoic acid production by *Schizochytrium limacinum* SR21, Article, 1998, 5 pages, pp. 72-76, Appl Microbiol Biotechnol.
Ruchi Jain et al., Extracellular Polysaccharide Production by Thraustochytrid Protists, Article, 2005, 9 pages, pp. 184-192, Marine Biotechnology, vol. 7.
S. Geresh et al., The Extracellular Polysaccharides of the Red Microalgae: Chemistry and Rheology, Article, 1991, pp. 195-201, Bioresource Technology 38.
T. Matsunaga et al., Sulfated extracellular polysaccharide production by the halophilic . . . , Article, 1996, pp. 24-27, Appl Microbiol Biotechnol.
Kenichi Sogawa et al., Marine microalgal polysaccharide induces apoptosis in human lymphoid cells, Article, 1998, pp. 35-38, J Mar Biotechnol.
Pratima Bajpai et al., Eicosapentaenoic acid (EPA) production from microorganisms: a review, Article, 1993, pp. 161-183, Journal of Biotechnology.
W.R. Barclay et al., Heterotrophic production of long chain omega-3 fatty acids utilizing algae and algae-like microorganisms, Article, 1994, pp. 123-129, Journal of Applied Phycology.
Tom E. Lewis et al., The Biotechnological Potential of Thraustochytrids, Article, 1999, pp. 580-587, Marine Biotechnology.
James G. Wallis et al., Polyunsaturated fatty acids syhthesis: what will they think of next?, Article, Sep. 2002, 7 pages, TRENDS in Biochemical Sciences vol. 27 No. 9.
Kim E. Harrison, The Role of Nutrition in Maturation, Reproduction and Embryonic Development of Decapod Crustaceans: A Review, Article, 1990, pp. 1-28, Journal of Shellfish research, vol. 9.

* cited by examiner

*Primary Examiner* — Irene Marx
(74) *Attorney, Agent, or Firm* — Reinhart Boerner Van Deuren P.C.

(57) ABSTRACT

The present disclosure provides a novel mutant strain of *Schizochytrium limacinum* having the Accession No. MTCC 5249, which produces lipids and extracellular polysaccharide (EPS) simultaneously. The disclosure further provides a process for simultaneous production of lipids and extracellular polysaccharide (EPS) from the novel mutant strain of *Schizochytrium limacinum*. The lipids produced from the novel mutant strain of *Schizochytrium limacinum* comprises docosahexaenoic acid (DHA). The disclosure also provides a food, feed, cosmetic, nutritional or therapeutic supplement for humans or animals comprising the cell biomass and extracellular polysaccharides (EPS) of the mutant strain of *Schizochytrium limacinum*. A cosmetic composition comprising the extracellular polysaccharides (EPS) of *Schizochytrium limacinum* is also provided that is useful as a base for cosmetics for topical application. The present disclosure further provides a pickle composition and a fat product having improved nutritive value.

9 Claims, No Drawings

STRAIN OF *SCHIZOCHYTRIUM LIMACINUM* USEFUL IN THE PRODUCTION OF LIPIDS AND EXTRACELLULAR POLYSACCHARIDES AND PROCESS THEREOF

CROSS-REFERENCE TO RELATED PATENT APPLICATIONS

This patent application is a Continuation of International Application No. PCT/IN2006/000508, filed Dec. 28, 2006, that claims priority to Indian Application No. 1720/CHE/2006, filed Sep. 20, 2006, and Indian Application No. 1719/CHE/2006, filed Sep. 20, 2006, and Indian Application No. 1948/CHE/2005, filed Dec. 29, 2005, the entire teachings and disclosure of which are incorporated herein by reference thereto.

TECHNICAL FIELD OF INVENTION

The present disclosure relates to a novel mutant strain of *Schizochytrium limacinum*. The disclosure further provides a process for the simultaneous production of lipids and extracellular polysaccharides (EPS) from the novel mutant strain of *Schizochytrium limacinum*.

BACKGROUND OF THE INVENTION

Fatty acids are constituents of fats and lipids. Fats and lipids are found in all living organisms and are essential for their growth, survival and reproduction. Saturated fatty acids are those in which all the carbon bonds in the molecule are connected to each other only by single bonds. Unsaturated fatty acids contain carbon atoms, one or more of which are connected by double bonds. Fatty acids with more than one double bond are called polyunsaturated fatty acids (PUFAs). PUFAs vary in the position of the first double bond from the methyl end of the fatty acid molecule, the number of carbon atoms in the fatty acid and the number of double bonds. PUFAs in which the double bond occurs at the third carbon from the methyl end of the fatty acid molecule are called omega-3 fatty acids. Examples are docosahexaenoic acid (DHA) and eicosapentaenoic acid (EPA), DHA contains 22 carbon atoms and 6 double bonds. It is represented as 22:6w3 EPA contains 20 carbon atoms and 5 double bonds, it is represented as 20:5w3 (Wailis, J. G. et al. 2002. Trends in biochemical Sciences 27: 467-473). Several of the PUFAs are extremely important for human health. DHA is extremely important in the brain development of infants, retinal vision, prevention of cardiovascular and many other disease states (Bajpai P. and P. K. Baipai. 1993. Journal of Biotechnology 30: 161-183; Barclay, W. R. et al. 994. Journal of Applied Psychology 6: 123-129; U.S. Pat. No. 9,428,913). DHA is known to be important in development, maturation and reproduction of crustaceans, including many animals of importance in aquaculture such as prawns (Harrison, K. E. 390, Journal of Shellfish Research, 9: 1-28). Therefore, it is important to incorporate DHA and EPA in human and animal foods.

Polysaccharides are polymers of different kinds of sugars. Many polysaccharides are of biotechnological use. Thus, for example, cellulose and starch are polymers of glucose, while agar-agar, which is used in jellies and for microbiology research, is a polymer produced by the marine sea weeds, the red algae. The marine sea weeds, the brown algae produce the polysaccharides alginates. Polysaccharides are produced by a wide variety of plants, animals and microorganisms. Microorganisms such as cyanobacteria, heterotrophic bacteria and fungi produce polysaccharides which are secreted out into the growth medium outside their cells. Polysaccharides thus secreted out into the liquid culture growth medium are called extracellular polysaccharides (EPS). There are several examples of the biotechnological uses of EPS.

Many such polysaccharides contain sulphate groups and are termed sulphated polysaccharides. Sulfated polysaccharides are also of biotechnological importance, for example, as blood anticoagulants and antiviral compounds (K. Sogawa et al., 1998, Marine microalgal polysaccharides induces apoptosis in the human lymphoid cells. Journal of Marine Biotechnology 6:35-38). Several papers have described the application of extracellular sulfated polysaccharides from organisms such as the cyanobacterium *Aphanocapsa halophytia* and the red alga *Porphyridium* sp. (S. Geresh and S. Arad, 1991, Bioresource Technology 38: 195-201; T. Matsunaqa et al., 1998, Applied Microbiology and Biotechnology 45: 24-27). Sulphated polysaccharides thus have the potential for various applications.

Thraustochytrids are unicellular marine organisms that are heterotrophic. i.e., they require organic carbon for their nutrition similar to fungi and bacteria.

The major genera are *Thraustochytrium, Schizochytrium* and *Ulkenia*, which correspond in morphology to cultures deposited at the American Type Culture Collection bearing Accession Nos. ATCC 28210, 24473, 34304, 28209 and MYA-1381. The major current commercial sources for the production of DNA are fish oil single-celled algae and the single-celled protists, the thraustochytrids. Thraustochytrids are now known to be commercially important for the production of the polyunsaturated fatty acid and docosahexadnoic acid (DHA). The biotechnological importance of thraustochytrids for the production of DHA has been reviewed by Lewis et al. (Lewis, T. E, et al. 1999. Marine Biotechnology 1: 580-587).

U.S. Pat. Nos. 5,130,242, 5,340,742 and 5,340,594 describe a process for the production of whole cells or products extracted from whole cells of thraustochytrids with high amounts of DHA, which can be used to supplement processed foods as a nutritional supplement, or to fish and animal feeds to enhance DHA contents and to use the extracted products in nutritional pharmaceutical and industrial applications. However, this patent does not encompass using the spent culture filtrate for the production of any products, including extracellular polysaccharides. These patents describe the process of growing thraustochytrids but it does not teach the simultaneous production of lipids and extracellular polysaccharides.

Japanese Patent No. 9633263 (1966) describes a strain of a thraustochytrids, which can be grown in fermentors, the cell biomass harvested can be used for application in the food industry such as food additives, nutritional supplements as additives for infant milk formula, feedstuffs and drug additives, where an addition of DHA is resulted because the cells have high amounts of DHA. However, this patent also does not encompass using the spent culture filtrate for the production of any products, including extracellular polysaccharides.

The U.S. Pat. Nos. 5,518,918, 5,688,500, 5,908,622, 6,103,225, 6,566,123 5,374,657 and 5,550,156 and the European Patent EP 0669809 disclose a process for growing thraustochytrids in a growth medium containing non-chloride containing salts, such that cell aggregates are produced which are useful as food products in aquaculture. Each of these patents discusses different compositions of the aquaculture feed. However, these patents do not encompass using the spent culture filtrate for any products, including extracellular polysaccharides. These patents describe the process of growing thraustochytrids but it does not teach the simultaneous production of lipids and extracellular polysaccharides.

The U.S. Pat. Nos. 5,985,348 and 6,177,108 disclose a process for growing thraustochytrids in a culture medium, harvesting the whole cell biomass and feeding the biomass or oils extracted from them to milk producing animals to enhance DHA contents in milk produced from them. However, these patents do not encompass using the spent culture filtrate for any products, including extracellular polysaccharides.

The U.S. Pat. Nos. 6,054,147, 6,716,460 and the European Patent. EP1021083 disclose a feeding regime for increasing omega-3 fatty acids in poultry meat or to improve the flavor, tenderness and overall consumer acceptability of poultry meat by feeding poultry animals with cell biomass or oils extracted from the cell biomass of thraustochytrids grown in suitable nutrient media. However, the patents do not encompass using the spent culture filtrate for the production of any products, including extracellular polysaccharides.

The U.S. Pat. Nos. 6,582,941 and 6,607,900 relates to a strain of thraustochytrids which produces a high amount of the omega-3 fatty acid docosapentaenoic acid in their cell biomass, whereby the organism is grown in suitable nutrient media and the cell biomass, or extracts of the cell biomass with the fatty acid can be used in composition of various feedstuffs for increasing the contents of docosapentaenoic acid. However, the patents do not encompass using the spent culture filtrate for any products, including extracellular polysaccharides. These patents do not teach the present invention.

Thus, in all the above prior art known processes relating to the production of DHA from thraustochytrids, the spent culture medium is discarded. Particularly, the culture filtrate is not used for the production of commercially useful extracellular polysaccharides (EPS). Therefore their use is limited to the preparation of only a single product.

Thus, in all the above mentioned known prior art processes relating to the production of commercially useful extracellular polysaccharides from various microorganisms, the cell biomass is discarded. Particularly, the cell biomass is not used for the production of the polyunsaturated fatty acid, DHA. Therefore, their use is limited to the preparation of only a single product.

Except as otherwise indicated, the disclosure of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the subject matter of the present invention.

SUMMARY OF THE INVENTION

The present disclosure relates to a mutant strain of Schizochytrium limacinum belonging to thraustochytrids having the Accession No. MTCC 5249 designated as 16(−2) capable of producing lipids and extracellular polysaccharide (EPS) simultaneously. The disclosure further provides a process for the simultaneous production of lipids and extracellular polysaccharides from the novel strain of Schizochytrium limacinum.

One aspect of the disclosure is to provide a mutant strain of Schizochytrium limacinum having the Accession No. MTCC 5249 capable of producing lipids and extracellular polysaccharide (EPS) simultaneously.

Another aspect of the disclosure provides a process for simultaneous production of lipids and extracellular polysaccharides (EPS) from the novel mutant strain of Schizochytrium limacinum, the process comprises:
culturing the cells of novel mutant strain of Schizochytrium limacinum having the Accession No. MTCC 5249 in a culture medium having pH in the range of 5.0-9.0;
incubating the cells at a temperature in the range of 25-37° C. for a period of 3-7 days to obtain a culture;
obtaining cell biomass and culture filtrate from the culture;
extracting lipids from said cell biomass; and
extracting extracellular polysaccharides (EPS) from the culture filtrate using solvents.

Yet another aspect of the disclosure provides a food, feed, cosmetic, nutritional or therapeutic supplements comprising the cell biomass of the novel mutant strain of Schizochytrium limacinum having the Accession No. MTCC 5249.

Still another aspect of the disclosure provides a food or cosmetic lipid composition comprising the lipids obtained from the cell biomass of Schizochytrium limacinum having the Accession No. MTCC 5249.

Still yet another aspect of the disclosure provides a food, feed, nutritional or therapeutic supplements comprising the extracellular polysaccharides (EPS) obtained from Schizochytrium limacinum having the Accession No. MTCC 5249.

Another aspect of the disclosure provides a cosmetic composition comprising the extracellular polysaccharides (EPS) obtained from Schizochytrium limacinum having the Accession No. MTCC 5249, this composition is also used as a base for cosmetics.

Yet another aspect of the disclosure provides a pickle composition having improved nutritive value comprising:
DHA extracted from the cell biomass of the novel mutant strain of Schizochytrium limacinum having the Accession No. MTCC 5249;
pickle stock; and
spices.

Still another aspect of the disclosure provides a fat product with high nutritive value comprising DHA extracted from the cell biomass of the novel mutant strain of Schizochytrium limacinum having the Accession No. MTCC 5249, wherein said fat product is selected from a group consisting of margarine, mayonnaise, butter, clarified butter, dressing or edible oil.

DETAILED DESCRIPTION OF THE INVENTION

The present disclosure particularly relates to a process for the simultaneous preparation of lipids and extracellular polysaccharides (EPS) from novel mutant strain of marine protists belonging to the order thraustochytrids, Genus Schizochytrium and Species limacinum.

In one aspect of the disclosure, four mutants were identified that showed enhanced DHA activity. Out of these four mutant strains, one mutant strain designated as 16(−2) was identified as the best mutant strain as it produced high content of DHA. This novel mutant strain designated as 16(−2) produces high level of DHA, i.e., 25-30% as compared to the wild type. This mutant strain produces 5-12 g/l of DHA, more preferably 8-12 g/l, most preferably 10-12 WI. Whereas, the wild type Schizochytrium limacinum produces about 5 g/l DHA. The lipids produced by the novel mutant strain comprise myristic acid, palmitic acid, oleic acid, linoleic acid, docosapentaenoic acid (DPA) and docosahexaenoic acid (DHA).

Presence of EPS in the culture filtrates were analyzed in the wild type and in the novel mutant strain of *Schizochytrium limacinum* using methods well known in the art. Quantitative estimation of EPS showed the presence of sulphated polysaccharides at higher level as compared to the wild type strain. It was found that the novel mutant strain of *Schizochytrium limacinum* produced EPS in the range of 1-2.5 g/l, preferably 1.5 g/l. The composition of the polysaccharides was analyzed for the presence of different monosaccharides. The monosaccharides identified were galactose, mannose, arabinose and fucose or rhamnose. It was found that the level of galactose was highest among all the monosaccharides. The mutant strain produced about 1.5 times more EPS as compared to the wild type.

The present disclosure further provides a novel mutant strain of *Schizochytrium limacinum* belonging to thraustochytrids having the Accession No. MTCC 5249 capable of producing lipids and extracellular polysaccharides (EPS) simultaneously. The two products, namely the lipids and the extracellular polysaccharides (BPS) are produced simultaneously in substantial amounts from a single novel mutant strain of *Schizochytrium limacinum*. The disclosure further provides a process for the simultaneous production of lipids and extracellular polysaccharides from the novel mutant strain of *Schizochytrium limacinum*, wherein the process produces 5-12 g/l DHA, preferable 8-12 g/l and 1-2.5 g/l EPS, preferably 1.58/l.

In another aspect, the present disclosure provides a process for the preparation of a novel organism belonging to *Schizochytrium limacinum* designated as MTCC 5249 useful for the simultaneous preparation of docosahexaenoic acid (DHA) an extracellular polysaccharide (EPS). The soil samples were taken from the intertidal beach located at Manappadu Beach, Tuticorin District, India in a solid culture medium consisting of an organic carbon source, a nitrogen source, a vitamin source, seawater and agar, and also a source of an antibiotic to prevent bacterial growth.

The novel mutant strain of *Schizochytrium limacinum* has been deposited at the Microbial Type Culture Collection at the Institute for Microbial Technology, an Institution under Council of Scientific & industrial Research (CSIR) Sector 39-1, Chandigrah India as required under the Provision to Section 10 (4) (ii) of the Patents Act, 70 and has been given the Accession No. MTCC 5249 and was deposited on 18.10.2005. The subject strains have been deposited under conditions that assure that access to the cultures will be available during the pendency of this patent application to one determined by the Commissioner of Patents and Trademarks to be entitled thereto wlder 37 CFR 1.14 and 35 U.S.C. 122. The deposit will be available as required by foreign patent laws in countries wherein counterparts of the subject application, or its progeny, are filed. However, it should be understood that the availability of a deposit does not constitute a license to practice the subject invention in derogation of patent rights granted by governmental action. Further, the subject deposits will be stored and made available to the public in accord with the provisions of the Budapest Treaty for the Deposit of Microorganisms, i. e., it will be stored with all the care necessary to keep it viable and uncontaminated for a period of at least five years after the most recent request for the furnishing of a sample of the deposit, and in any case, for a period of at least thirty (30) years after the date of deposit or for the enforceable life of any patent which may issue disclosing the culture. The depositor acknowledges the duty to replace the deposit should the depository be unable to furnish a sample when requested, due to the condition of the deposit.

All restrictions on the availability to the public of the subject culture deposit will be irrevocably removed upon the granting of a patent disclosing it.

The terms "MTCC 5249" and "16(−2)" are used interchangeable hereinafter and refer to the novel mutant strain of *Schizochytrium limacinum*. The novel mutant strain of *Schizochytrium limacinum* (MTCC 5249) is useful for producing lipids and polysaccharides simultaneously that have nutraceutical or nutritional and/or pharmaceutical applications. The novel mutant strain of *Schizochytrium limacinum* (MTCC 5249) is useful for producing lipids and polysaccharides simultaneously that have cosmetic applications.

The lipids produced by the disclosed process comprise myristic acid, palmitic acid, oleic acid, linoleic acid, docosapentaenoic acid (DPA) and docosahexaenoic acid (DNA). These lipids are useful for human health, for prevention of various diseases such as cardiovascular and inflammatory diseases and in infant nutrition for proper brain development and retinal vision in children. The extracellular polysaccharides (EPS) prepared by the process of the present disclosure are useful as antiviral agents and in cosmetics as gels.

One embodiment of the present disclosure provides a novel mutant strain of *Schizochytrium limacinum* having the Accession No. MTCC 5249 that produces lipids and extracellular polysaccharides (EPS) simultaneously.

Another embodiment of the present disclosure provides a novel mutant strain, wherein the lipid comprises myristic acid, palmitic acid, oleic acid, linoleic acid, docosapentaenoic acid (DPA) and docosahexaenoic acid (DHA).

Yet another embodiment of the present disclosure provides a novel mutant strain, wherein the extracellular polysaccharides (EPS) comprises sulphated polysaccharides.

Still another embodiment of the present disclosure provides a process for simultaneous production of lipids and extracellular polysaccharides (EPS) from the novel mutant strain of *Schizochytrium limacinum*, wherein said process comprises:
culturing the cells of novel mutant strain of *Schizochytrium limacinum* having the Accession No. MTCC 5249 in a culture medium having pH in the range of 5.0-9.0;
incubating the cells at a temperature in the range of 25-37° C. for a period of 3-7 days to obtain a culture;
obtaining cell biomass and culture filtrate from the culture;
extracting lipids from said cell biomass; and
extracting extracellular polysaccharides (EPS) from the culture filtrate using solvents.

Yet another embodiment of the present disclosure provides a process for simultaneous production of lipids and extracellular polysaccharides (EPS) from the novel mutant strain of *Schizochytrium limacinum*, wherein said lipids comprise myristic acid, palmitic acid, oleic acid, linoleic acid, docosapentaenoic acid (DPA) and docosahexaenoic acid (DHA).

Still yet another embodiment of the present disclosure provides a process for simultaneous production of lipids and extracellular polysaccharides (EPS) from the novel mutant strain of *Schizochytrium limacinum*, wherein the concentration and docosahexaenoic acid (DHA) is in the range of 25-45%.

Another embodiment of the present disclosure provides a process for simultaneous production of lipids and extracellular polysaccharides (EPS) from the novel mutant strain of *Schizochytrium limacinum*, wherein said extracellular polysaccharide (EPS) comprises sulphated polysaccharide.

Yet another embodiment of the present disclosure provides a process for simultaneous production of lipids and extracellular polysaccharides (EPS) from the novel mutant strain of

*Schizochytrium limacinum*, wherein said culture medium comprises an organic carbon source, a nitrogen source and a vitamin source.

Still yet another embodiment of the present disclosure provides a process for simultaneous production of lipids and extracellular polysaccharides (EPS) from the novel mutant strain of *Schizochytrium limacinum*, wherein the organic carbon source is selected from a group consisting of glucose, cotton seed flour, starch, glycerol, molasses and corn steep liquor.

Another embodiment of the present disclosure provides a process for simultaneous production of lipids and extracellular polysaccharides (EPS) from the novel mutant strain of *Schizochytrium limacinum*, wherein the nitrogen source is selected from a group consisting of peptone, corn steep liquor, yeast extract, ammonium sulphate and ammonium nitrate.

Yet another embodiment of the present disclosure provides a process for simultaneous production of lipids and extracellular polysaccharides (EPS) from the novel mutant strain of *Schizochytrium limacinum*, wherein the vitamin source is selected from a group consisting of yeast extract, corn steep liquor, beef extract, malt extract and soy extract.

Still yet another embodiment of the present disclosure provides a process for simultaneous production of lipids and extracellular polysaccharides (EPS) from the novel mutant strain of *Schizochytrium limacinum*, wherein said carbon source is in the range of 0.5-10% w/v.

Another embodiment of the present disclosure provides a process for simultaneous production of lipids and extracellular polysaccharides (EPS) from the novel mutant strain of *Schizochytrium limacinum*, wherein said nitrogen source is in the range of 0.1-5% w/v.

Yet another embodiment of the present disclosure provides a process for simultaneous production of lipids and extracellular polysaccharides (EPS) from the novel mutant strain of *Schizochytrium limacinum*, wherein said vitamin source is in the range of 0.1-1% w/v.

Still another embodiment of the present disclosure provides a process for simultaneous production of lipids and extracellular polysaccharides (EPS) from the novel mutant strain of *Schizochytrium limacinum*, wherein said temperature is preferably in the range of 25-32° C.

Still yet another embodiment of the present disclosure provides a process for simultaneous production of lipids and extracellular polysaccharides (EPS) from the novel mutant strain of *Schizochytrium limacinum*, wherein said solvent is selected from a group consisting of ethanol, tetrahydrofuran, isopropyl alcohol, diethylether, dichloromethane, chloroform and ethyl acetate.

Another embodiment of the present disclosure provides a food, feed, cosmetic, nutritional or therapeutic supplements comprising the cell biomass of the novel mutant strain of *Schizochytrium limacinum* having the Accession No. MTCC 5249.

Yet another embodiment of the present disclosure provides a food, feed, cosmetic, nutritional or therapeutic supplements comprises spray dried cell biomass of the novel mutant strain of *Schizochytrium limacinum* having the Accession No. MTCC 5249.

Still another embodiment of the present disclosure provides a food, feed, cosmetic, nutritional or therapeutic supplements, wherein said cell biomass comprises lipids.

Still yet another embodiment of the present disclosure provides a food, feed, cosmetic, nutritional or therapeutic supplements, wherein said lipids comprises myristic acid, palmitic acid, oleic acid, linoleic acid, docosapentaenoic acid (DPA) and docosahexaenoic acid (DHA).

Still yet another embodiment of the present disclosure provides a food, feed, cosmetic, nutritional or therapeutic supplements, the cell biomass is obtained by a process comprising:
    culturing the cells of novel mutant strain of *Schizochytrium limacinum* having the Accession No. MTCC 5249 in a culture medium having pH in the range of 5.0-9.0;
    incubating the cells at a temperature in the range of 25-37° C. for a period of 3-7 days to obtain a culture; and
    obtaining cell biomass from the culture.

Another embodiment of the present disclosure provides a food or cosmetic lipid composition comprising the lipids obtained from the cell biomass of *Schizochytrium limacinum* having the Accession No. MTCC 5249.

Another embodiment of the present disclosure provides a food or cosmetic lipid composition, wherein said lipids comprises myristic acid, palmitic acid, oleic acid, linoleic acid, docosapentaenoic acid (DPA) and docosahexaenoic acid (DHA).

Yet another embodiment of the present disclosure provides a food, feed, nutritional or therapeutic supplements comprising the extracellular polysaccharides (EPS) obtained from *Schizochytrium limacinum* having the Accession No. MTCC 5249.

Still yet another embodiment of the present disclosure provides a food, feed, nutritional or therapeutic supplements comprising the extracellular polysaccharides (EPS) obtained from *Schizochytrium limacinum* having the Accession No. MTCC 5249, wherein said extracellular polysaccharides (EPS) comprises sulphated polysaccharides.

Another embodiment of the present disclosure provides a food, feed, nutritional or therapeutic supplements comprising the extracellular polysaccharides (EPS) obtained from *Schizochytrium limacinum* having the Accession No. MTCC 5249, wherein said extracellular polysaccharides (EPS) are obtained by a process comprising:
    culturing the cells of novel mutant strain of *Schizochytrium limacinum* having the Accession No. MTCC 5249 in a culture medium having pH in the range of 5.0-9.0;
    incubating the cells at a temperature in the range of 25-37° C. for a period of 3 to 7 days to obtain a culture;
    obtaining cell biomass and culture filtrate from the culture; and
    extracting extracellular polysaccharides (EPS) from the culture filtrate using solvents.

Another embodiment of the present disclosure provides a cosmetic composition comprising the extracellular polysaccharides (EPS) obtained from *Schizochytrium limacinum* having the Accession No. MTCC 5249, wherein said composition is used as a base for cosmetics.

Yet another embodiment of the present disclosure provides a cosmetic composition comprising the extracellular polysaccharides (EPS) obtained from *Schizochytrium limacinum* having the Accession No. MTCC 5249, wherein said extracellular polysaccharides comprises sulphated polysaccharides.

Another embodiment of the present disclosure provides a pickle composition having improved nutritive value comprising:
    DHA extracted from the cell biomass of the novel mutant strain of Schizochytrium limacinum having the Accession No. MTCC 5249;
    pickle stock; and
    spices.

Yet another embodiment of the present disclosure provides a pickle composition having improved nutritive value, wherein the concentration of the DHA is in the range of 0.2-3%.

Still another embodiment of the present disclosure provides a pickle composition having improved nutritive value, wherein the pickle stock is selected from a group consisting of fruits, vegetables, meat and fish in salt with oil.

Still yet another embodiment of the present disclosure provides a pickle composition having improved nutritive value, wherein the spices are selected from a group consisting of aniseeds, asafetida, cumin seeds, cardamom, cinnamon, clove, fenugreek seeds, flower essence, mace, mango powder and mustard seeds.

Another embodiment of the present disclosure provides a fat product with high nutritive value comprising DHA extracted from the cell biomass of the novel mutant strain of *Schizochytrium limacinum* having the Accession No. MTCC 5249, wherein said fat product is selected from a group consisting of margarine, mayonnaise, butter, clarified butter, dressing or edible oil.

Still yet another embodiment of the present disclosure provides, a fat product with high nutritive value comprising DHA extracted from the cell biomass of the novel mutant strain of *Schizochytrium limacinum* having the Accession No. MTCC 5249, wherein the concentration of the DHA, is in the range of 0.2-3%.

Another embodiment of the disclosure further provides a process for growing the mutant strain *Schizochytrium limacinum* having Accession No. MTCC 5249, wherein said process comprises:

culturing soil on a culture medium comprising a carbon source, a nitrogen source, a vitamin source, seawater and agar and antibiotic;

transferring the cells to a fresh liquid culture medium comprising nitrogen source, a vitamin source, seawater and antibiotic;

spreading the culture containing the cells obtained in the previous step on said culture medium used;

exposing the cells to ultraviolet light for varying period in the range of 1-10 minutes; and separating the cells.

Yet another embodiment of the disclosure provides the process for growing the mutant strain of *Schizochytrium limacinum* having Accession No. MTCC 5249, wherein the carbon source used in the medium is selected from a group consisting of glucose, starch, glycerol, molasses and corn steep liquor.

Still yet another embodiment of the disclosure provides the process for growing the mutant strain of *Schizochytrium limacinum* having Accession No. MTCC 5249 and mutant strain derived therefrom, wherein the concentration of the carbon source is in the range of 0.5-10%.

Still yet another embodiment of the disclosure provides the process for growing the mutant strain *Schizochytrium limacinum* having Accession No. MTCC 5249, wherein the nitrogen source used in the medium is selected from a group consisting of peptone, corn steep liquor, yeast extract and ammonium nitrate.

Still yet another embodiment of the disclosure provides the process for growing the mutant strain of *Schizochytrium limacinum* having Accession No. MTCC 5249, wherein the concentration of the nitrogen source is in the range of 0.1-5%.

Various lipids have been extracted from the cell biomass obtained from the mutant strain of *Schizochytrium limacinum* having Accession No. MTCC 5249. These lipids are myristic acid, palmitic acid, oleic acid, linoleic acid, docosapentaenoic acid (DPA) and docosahexaenoic acid (DHA). No docosahexaenoic acid (DHA) producing organisms, particularly those belonging to *Schizochytrium limacinum*, have been known to be used simultaneously for the production of docosahexaenoic acid (DHA) from cell biomass and biotechnologically useful extracellular polysaccharides (EPS) from the culture filtrate. Particularly, no strain belonging to the group Thraustochytrids has been known to produce docosahexaenoic acid (DHA) and extracellular polysaccharides (EPS) simultaneously. The present disclosure provides a mutant strain of *Schizochytrium limacinum* having Accession No. MTCC 5249, capable of producing docosahexaenoic acid (DHA) above 5.0 g/L and commercially feasible amounts of EPS above 1g/L simultaneously.

In another aspect, the present disclosure provides a process for the preparation of a novel organism belonging to *Schizochytrium limacinum* designated as MTCC 5249 useful for the simultaneous preparation of docosahexaenoic acid (DHA) and extracellular polysaccharide (EPS) which comprises:

culturing soil samples from intertidal beach located at Manappadu Beach, Tuticorin District, India in a solid culture medium consisting a carbon source, a nitrogen source, a vitamin source, seawater and agar, and also a source of an antibiotic to prevent bacterial growth;

removing the colonies formed to a fresh liquid culture medium containing all the above mentioned sources expect agar to get cultures containing cells;

spreading the culture containing the cells in the solid culture medium;

exposing the cells thus spread to ultraviolet light for varying period in the range of 1 to 10 minutes; and separating the novel micro organism formed by conventional methods.

In yet another aspect, the present disclosure provides a process for the simultaneous preparation of docosahexaenoic acid and extracellular polysaccharide (EPS) comprising:

culturing the mutant strain of *Schizochytrium limacinum* designated as MTCC 5249 in a culture medium containing an organic carbon source, a nitrogen source and a vitamin source at a pH in the range of 5.0 to 8.0;

Incubating the culture at a temperature in the range of 25-37° C. for a period in the range of 3 to 7 days;

separating the cell biomass containing lipids like docosahexaenoic acid (DHA) obtained from the cell biomass by conventional methods;

extracting docosahexaenoic acid (DHA) from the cell biomass by known solvent extraction method; and treating the culture filtrate containing the extracellular polysaccharides (EPS) obtained in the above step by conventional methods.

In one aspect, the carbon source is selected from a group consisting of glucose, starch, glycerol, molasses and corn steep liquor.

In another aspect, the nitrogen source selected from a group consisting of peptone, corn steep liquor, yeast extract and ammonium nitrate.

In another aspect, the vitamin source is selected from a group consisting of yeast extract and corn steep liquor.

In yet another aspect, the amounts of these sources can vary from 0.5 to 10% in the case of the carbon source, 0.1 to 5% in the case of the nitrogen source and 0.1 to 5% in the case of the vitamin source.

In another aspect, the cultures may be grown in suitable volumes and vessels, ranging from 100 ml to several thousands of liters, in flasks or large fermentors, using various nutrient media containing a carbon, nitrogen and vitamin source as above.

In yet another aspect, the separation of the cell biomass containing lipids like docosahexaenoic acid (DHA) may be affected by centrifugation, filtration and flocculation etc. The cell biomass thus obtained containing lipids like docosahexaenoic acid (DHA) may also be spray-dried and directly used in animal feeds.

In yet another aspect, the precipitation of the extracellular polysaccharides (BPS) is performed using an alcoholic solvent like ethanol or other suitable reagents and drying. The EPS thus obtained can then be commercially used in formulations as antiviral agents or in cosmetic formulations.

In yet another aspect, a single culture process is used for producing both lipids and sulphated polysaccharides, instead of using two separate processes thereby making the process economical and simple. Both the cell biomass, as well as the culture filtrate are used fruitfully thus minimizing wastage of these materials as well as avoiding disposal and environmental problems.

A novel organism belonging to the thraustochytrids is made available which is useful for producing simultaneously docosahexaenoic acid in more than 5 g/L and extracellular polysaccharides in more than 1 g/L instead of using two separate organisms. Such a commercially applicable process makes the process not only simple but also economical.

A single culture process is used for producing both polyunsaturated fatty acids and sulphated polysaccharides, instead of using two separate processes thereby making the process economical and simple.

Both the cell biomass as well as the spent culture medium are used fruitfully thus minimizing wastage of these materials as well as avoiding disposal and environmental problems. The process not only adds value to the process but also results in an economical use of process.

One embodiment describes the process for the preparation of the mutant strain of *Schizochytrium limacinum* designated as MTCC 5249, for details see example 1.

Young cells of *Schizochytrium limacinum* measured approximately 4-6 μm and were produced by encycted zoospores in MV broth. The cells enlarged and the contents became granular upon maturation. Mature cells were globular and measured 10.0-14.0 μm in diameter. Each cell divided further into 8 individual cells which initially measured 6-8 μm in diameter. Such cells also separated from each other. These cells measured 10.0-14.0 μm in diameter when mature. Two different life cycles were observed thereafter. Zoospore formation was initially marked by the appearance of an undulated outer margin of the zoosporangial contents. Subsequent zoospore cleavage took place rapidly and the outlines of the zoospores could be clearly discerned. The zoospore showed rapid movements inside the zoosporangium for a very short period before being released. A total of 8 zoospores were produced by each zoosporangium. In the second type of development, each cell of the octad gradually assumed an irregular shape and transformed into limaciform amoebae, which became increasingly motile. The amoebae ranged in size from 3-6 μm×20-35 μm in size and had a granular content. Subsequently the limaciform amoebae rounded up into cells of about 10 μm in diameter. These transformed into zoosporangia as in the earlier case. Zoospore development, release and the number were similar as above. Zoospores were elliptical and had two subterminally attached heterokont flagella. The zoospores ranged from 5-7 μm×3-4 μm in size. Colonies on MV agar were spherical, white, globose, and glistening. The cells were globose to irregular in shape. The cells formed prominent, dense ectoplasmic nets.

Another embodiment describes the process for simultaneous production of cell biomass and extracellular polysaccharides (EPS) from the mutant strain of *Schizochytrium limacinum* designated as MTCC 5249, for detailed description see Example 2.

Yet another embodiment relates to the estimation of the lipids using Gas Chromatography in biomass of the mutant strain of *Schizochytrium limacinum*. For details see Example 3.

Still yet another embodiment relates to the estimation of the extracellular polysaccharides (EPS) the mutant strain of *Schizochytrium limacinum*. For details see Example 4.

Yet another embodiment relates to analysis of anti viral activity (Anti Hepatitis B) of exopolysaccharides from *Schizochytrium limacinum*. For details see Example 5.

Yet another embodiment relates to a pickle having improved nutritive value was prepared by method well known in the art. The pickle having improved nutritive value comprises omega 3 fatty acids like docosahexaenoic acid (DHA) and eicosapentaenoic acid (EPA), where DHA is extracted from the novel mutant strain of *Schizochytrium limacinum*. Spices and materials such as redchillies, tamarind, cuminseeds, uraddal, asafoetida, turmeric, ginger, garlic, green chillies, fenugreek, ground mustard, oil, salt, cloves, cumin seeds, cinnamon pepper powder and omega 3 fatty acids were used along with other ingredients well known in the art. For details see Example 6.

Yet another embodiment relates to fat products such as margarine, mayonnaise, butter, clarified butter, dressing or edible oil having improved nutritive value were prepared by methods well known in the art. The fat product having improved nutritive value comprises omega 3 fatty acids like DHA, where DHA is extracted from the novel mutant strain of *Schizochytrium limacinum*.

Shelf-stable clarified butter containing polyunsaturated fatty acids like docosahexaenoic acid (DHA) was prepared by methods well known in the art. For details see Example 7.

While particular embodiments of the subject invention have been described, it will be obvious to those skilled in the art that various changes and modifications of the subject invention can be made without departing from the spirit and scope of the invention. In addition, while the present invention has been described in connection with certain specific embodiments thereof, it is to be understood that this is by way of illustration and not by way of limitation and the scope of the invention is defined by the claims which should be construed as broadly as the prior art will permit.

EXAMPLES

The following examples are put forth so as to provide those of ordinary skill in the art with a complete disclosure and the description of how to make and use the present invention, and are not intended to limit the scope of what the inventors regard as their invention nor are they intended to represent that the experiments below are all and only experiments performed.

Example 1

Process for the Preparation of the Mutant Strain of *Schizochytrium limacinum*

The soil samples obtained from intertidal area of Manappadu Beach, Tuticurin District Tamil Nadu, India were grown in MV (Modified Vishniac) broth (Perkins, F. O., Arch.

Microbial., 84, 95-118, 1972) which contains Glucose (2.0%), Peptone (0.1%) and Yeast Extract (0.015%). A dilute suspension of a 2 day old culture was spread-plated on to MV agar in Petri plates. The plates were stored in a refrigerator at approximately 10° C. for 4 hours, as a selection stress prior to UV exposure. The plates were then exposed to UV using a UV box. Four colonies were selected from the plate based on the cell size and were then sub cultured in Malt extract broth. Each individual culture was then analyzed for DHA contents. Four mutants were identified that showed enhanced DHA activity. Out of these four mutant strains, one mutant strain designated as 16(−2) was identified as the best mutant strain as it produced high content of DHA. This mutant strain has been used in the present disclosure and was deposited at the Microbial Type Culture Collection at the Institute for Microbial Technology, has been given the Accession no MTCC 5249. The terms "MTCC 5249" and "16(−2)" are used interchangeably and refer to the mutant strain of *Schizochytrium limacinum*.

Example 2

Process for Simultaneous Production of Biomass and Extracellular Polysaccharides (EI's) from the Mutant Strain of *Schigochytrium limacinum*

The cells of the mutant strain of *Schizochytrium limacinum* designated as MTCC 5249 were cultured in a culture medium containing an organic carbon source, a nitrogen source and a vitamin source at a pH 7 and the culture was incubated at a temperature in the range of 25-32° C. for 5 days. The spent culture medium is filtered to obtain a cell biomass containing lipids comprising Myristic acid, Palmito acid, Oleic acid, Linoleic acid, Docosapentanoic acid, Docosahexanoic acid. The filtrate thus obtained was extracted using isopropyl alcohol as a solvent.

Extracellular polysaccharides were obtained by treating the spent culture filtrate containing the extracellular polysaccharide obtained by conventional methods.

As a carbon source, any one of the following but not necessarily limited to these may be used: glucose, starch, glycerol, molasses and corn steep liquor.

Example 3

Estimation of the Lipids in Biomass of the Mutant Strain of *Schizochytrium limacinum*

The Gas Chromatography (GC) analysis of the total lipids from the isolates showed very interesting results. The highest percentage of fatty acid in the total lipids was clearly palmitic acid, which was 54-60% followed by DHA, which was about 25-32%. Small amounts of docosapentaenoic acid and linoleic acid were also present in the isolates. A very interesting feature observed was the high value of star PUFA, DHA in the mutant strain. The level of DHA was almost 1.5 times the values in wild type.

DHA is the most valuable PUFA from the novel mutant strain of *Schizochytrium limacinum*.

Example 4

Estimation of the Extracellular Polysaccharides (EPS) the Mutant Strain of *Schizochytrium limacinum*

Quantitative estimation of EPS in the culture filtrates studied simultaneously in the wild type and the novel mutant strain of *Schizochytrium limacinum* having accession number MTCC 5249 using methods well known in the art. The estimation showed noticeable levels of EPS. The composition of the polysaccharides was analyzed for the presence of different monosaccharides. The monosaccharides identified were galactose, mannose, arabinose and fucose or rhamnose. The mutant strain produced about 1.5 times more EPS as compared to the wild type, most preferably 10-12 g/l DHA.

The cultures showed characteristic sigmoid curve with a lag phase of 48-56 hours and reached the stationary phase after 90 hours. EPS production was seen at all stages but lagged behind growth. The concentration increased with age, reaching the highest values during the stationary phase. The concentration of the polymer did not show any decline during the 120 hours of growth. It is very clear that EPS production is positively correlated to the biomass production.

The total fraction of EPS produced by the novel mutant strains contained sugars, proteins, lipids and uronic acid. Sugars were the most abundant constituent in all three isolates comprising almost 53%. Sulphate contents were higher in 16(−2) mutant strain. EPS produced by the mutant were viscous in nature.

Gas chromatography analysis showed the presence of galactose, mannose, arabinose and fucose or rhamnose by the novel mutant strain of *Schizochytrium limacinum*. Galactose formed the major component of the polysaccharide. Mannose was present as a minor composition in the wild type but in the mutant variety it was present in a very significant level. Similarly rhamnose was present as a minor constituent in the wild type but in the mutant variety it was present in significant levels.

The solubility of EPS produced by wild type, 16(−2) strain in various solvents clearly indicate that the EPS dissolved best in distilled water.

Example 5

Binding Inhibition Assay

Anti viral activity (Anti Hepatitis B) of extra cellular polysaccharides from novel mutant strain of *Schizochytrium limacinum* having accession number MTCC 5249 was analyzed using methods well known in the art. EIA assay was used. It is based on the principle that when sample containing HBsAg is incubated with compound that is suspected of antiHBV property. If the suspected compound has antiHBV activity it blocks primary binding of HBsAg to the primary antiEBSAg Antibody coated to well and doesn't give color which is calculated by Optical Density by micro plate reader.

It was seen that when EPS Treated HBsAg is added to antiHBsAg monoclonal antibody coated micro plate it blocks binding of HBsAg to well which leads to decreased O.D. The above experiment showed that polysaccharide of *Schizochytrium* spp is having antiHBV activity.

Example 6

Pickle Preparation

The DHA produced from novel mutant strain of *Schizochytrium limacinum* having accession number MTCC 5249 was used to mix with pickle stock to produce pickles enriched with DHA. The pickle stock can be any conventional vegetable, mixed vegetable or fruit or chicken, fish, mutton, prawns, meat etc and was made into a DHA enriched pickle. The preferred pickle stock however is not specific to particular vegetables or fruits stock. There is no special limitation on the types of vegetables or fruits to be processed into pickle vegetables according to the present disclosure.

The basic process of pickle preparation is generally applicable by those of skilled in the art to any vegetable or fruit pickle stock that comprises:

- washing the vegetables and fruits and drying and cutting the vegetables of fruits followed by rubbing with salt;
- heating the oil and frying asafetida in it till it becomes brown;
- adding all the ground spices into the oil containing asafetida;
- adding vegetables or fruits to above followed by mixing;
- packing in the jar; and
- adding DHA produced from novel mutant strain of *Schizochytrium limacinum* to the oil and pouring this oil containing DHA in the jar containing vegetables or fruits with spices;
- shaking the above mix every other day for 5-15 days.

Example 7

Fat Products

Butter (traditional unsalted butter made by hard churning whole milk curd at room temperature) was placed in a metal vessel and was heated to 100-120° C. with constant stirring over low fire to evaporate the moisture. When practically all the moisture has been removed, any further heating was avoided by removing the vessel from the fire. After the residue has settled down on cooling the clear fat is decanted into suitable container. After cooling and sedimentation the clarified butter was filtered through muslin cloth to remove the sediment. To the filtered clarified butter, DHA produced from novel mutant strain of *Schizochytrium limacinum* having accession number MTCC 5249 was added and the mixture was heated again. The mixture was then cooled to obtain the granular texture. The clarified butter thus obtained can be packed in tin containers, glass bottles or plastic pouches.

What is claimed is:

1. A biologically pure culture of *Schizochytrium limacinum* strain having the Accession No. MTCC 5249, wherein the strain is capable of producing lipids and extracellular polysaccharides (EPS) simultaneously.

2. The strain according to claim 1, wherein the lipid comprises myristic acid, palmitic acid, oleic acid, linoleic acid, docosapentaenoic acid (DPA) and docosahexaenoic acid (DHA).

3. The strain according to claim 1, wherein the extracellular polysaccharides (EPS) comprises sulphated polysaccharides.

4. A process for the simultaneous production of lipids and extracellular polysaccharides (EPS) from the *Schizochytrium limacinum* strain of claim 1, said process comprising:
   a) culturing the cells of the strain in a culture medium having a pH in the range of 5.0-9.0, wherein said culture medium comprises an organic carbon source, a nitrogen source, and a vitamin source;
   b) incubating the cells at a temperature in the range of 25-37° C. for a period of 3-7 days to obtain a culture;
   c) obtaining cell biomass and culture filtrate from the culture;
   d) extracting lipids from said cell biomass; and
   e) extracting extracellular polysaccharides (EPS) from the culture filtrate using solvents.

5. The process according to claim 4, wherein said lipids comprise myristic acid, palmitic acid, oleic acid, linoleic acid, docosapentaenoic acid (DPA) and docosahexaenoic acid (DHA).

6. The process according to claim 5, wherein the concentration of docosahexaenoic acid (DHA) is in the range of 25-32%.

7. The process as according to claim 4, wherein said extracellular polysaccharide (EPS) comprises sulphated polysaccharide.

8. The process according to claim 4, wherein the organic carbon source is selected from a group consisting of glucose, cotton seed flour, starch, glycerol, molasses and corn syrup.

9. The process according to claim 4, wherein the nitrogen source is selected from a group consisting of peptone, corn steep liquor, yeast extract, ammonium sulphate and ammonium nitrate.

* * * * *

UNITED STATES PATENT AND TRADEMARK OFFICE
CERTIFICATE OF CORRECTION

PATENT NO. : 8,232,090 B2  
APPLICATION NO. : 12/163429  
DATED : July 31, 2012  
INVENTOR(S) : Issac Oomman Kollenmareth et al.

Page 1 of 1

It is certified that error appears in the above-identified patent and that said Letters Patent is hereby corrected as shown below:

Title Page: Item [75]:

Inventor name is incorrectly spelled "Issac Oomman Kallenmareth" should be correctly spelled "Issac Oomman Kollenmareth"

Signed and Sealed this
Eighteenth Day of September, 2012

David J. Kappos
*Director of the United States Patent and Trademark Office*